US00PP30904P2

(12) United States Plant Patent
Hansen

(10) Patent No.: US PP30,904 P2
(45) Date of Patent: Sep. 24, 2019

(54) X MANGAVE PLANT NAMED 'FRECKLES AND SPECKLES'

(50) Latin Name: ***Manfreda* x *Agave* hybrid**
Varietal Denomination: Freckles and Speckles

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,464

(22) Filed: Mar. 1, 2018

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/12
See application file for complete search history.

(56) References Cited

PUBLICATIONS

Plant Delights Nursery, Sep. 2017.*

* cited by examiner

*Primary Examiner* — Keith O. Robinson

(57) ABSTRACT

A new and unique X *Mangave* plant named 'Freckles and Speckles' characterized by compact habit and lanceolate foliage with medium green color and with high ultra violet light exposure developing grey-purple speckling and blushing in the distal portions. The yellowish flowers with burnt orange blushing on tall stiff stapes are suitable as a potted plant or for the garden and loaded with nectar for attracting hummingbirds or for use as a houseplant.

1 Drawing Sheet

Botanical classification: *Manfreda* x *Agave* hybrid.
Variety denomination: 'Freckles and Speckles'.

BACKGROUND OF THE INVENTION

The present invention relates to the new and distinct X *Mangave* plant, X *Mangave* 'Freckles and Speckles' hybridized on Apr. 18, 2014 by the inventor at a wholesale perennial nursery in Zeeland, Mich., USA as a cross between an unreleased proprietary hybrid known by the breeder code H10-02-01 as the female or seed parent and an unreleased proprietary hybrid known by the breeder code 12-06-01 as the male or pollen parent. Through trials at the same nursery the plant was referred to by the code 14-48-19. The new plant has been successfully asexually propagated initially in 2016 by division at the same nursery in Zeeland, Mich. and also by tissue culture. Both methods of asexual propagation systems have been found to produce stable and identical plants that maintain all the unique characteristics of the original plant in successive generations.

No plants of X *Mangave* 'Freckles and Speckles' have been sold, in this country or anywhere in the world, prior to the filing of this application, nor has any disclosure of the new plant been made prior to the filing of this application except that which was disclosed or sold within one year of the filing of this application, and was either derived directly or indirectly from the inventor.

BRIEF SUMMARY OF THE INVENTION

X *Mangave* 'Freckles and Speckles' differs from its parents as well as all other *Manfreda, Agave* and X *Mangave* known to the applicant. The most similar known X *Mangave* cultivar known to the inventor are: 'Spotty Dotty' U.S. Plant Pat. No. 29,917, 'Inkblot' U.S. Plant Pat. No. 29,431, 'Bad Hair Day' U.S. Plant Pat. No. 30,279, 'Pineapple Express' U.S. Plant Pat. No. 28,613 and 'Bloodspot' (not patented).

'Spotty Dotty' has broader more green leaves with more spotting and less purple blushing in high light intensity and a slightly more wavy leaf. 'Inkblot' has flatter growth habit, the leaves arch more, with larger spots and a more greyed-purple coloration to the leaf and the flowers are burgundy colored and not the yellowish flowers of 'Freckles and Speckles'. 'Bad Hair Day' has more narrow foliage with smaller and fewer spots, more arching to horizontal habit with burgundy flowers of greater number than the new plant. 'Bloodspot' is more compact in habit, the leaves are shorter, thicker and more fibrous than the new plant. 'Pineapple Express' is more upright in habit with more leaves per plant and does not get the purple blush of the new plant. The female parent has bright yellow flowers on heavier branched scapes and the foliage is broader than the new plant. The male parent has flatter habit, a non-branched scape with mahogany flowers and more narrow foliage than the new plant. Further comparison with the female parent and male parents is not possible as neither plants nor photographs have been maintained.

The new plant, 'Freckles and Speckles', is unique from all of these variegated *Agave*, X *Mangave* and *Manfreda* known to the inventor by the following combined traits:

1. Compact habit with 30 to 60 leaves at flowering;
2. Foliage lanceolate with small flexible marginal teeth;
3. Foliage develops burgundy speckling throughout on chartreuse leaves with purple blush over the top surface;

4. Moderate to rapid growth rate with good natural pup production;
5. Yellowish flowers on stiff, tall, lightly-branched stapes.

BRIEF DESCRIPTION OF THE DRAWINGS

The photograph of the new plant demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
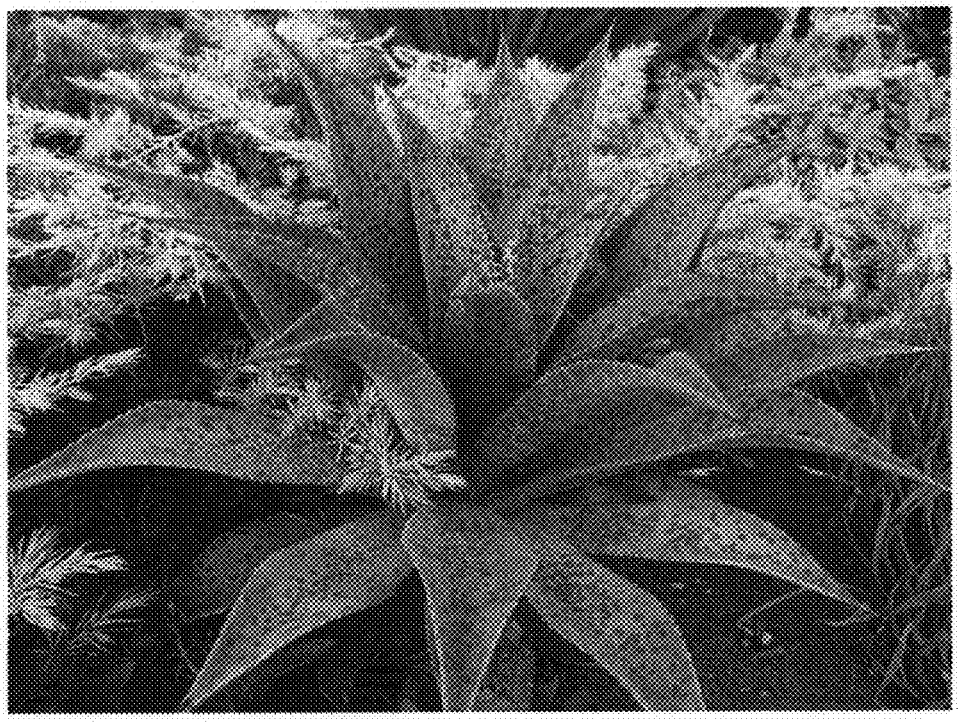
FIG. 1 shows the new plant in a container with base of scape.
Figure 2:
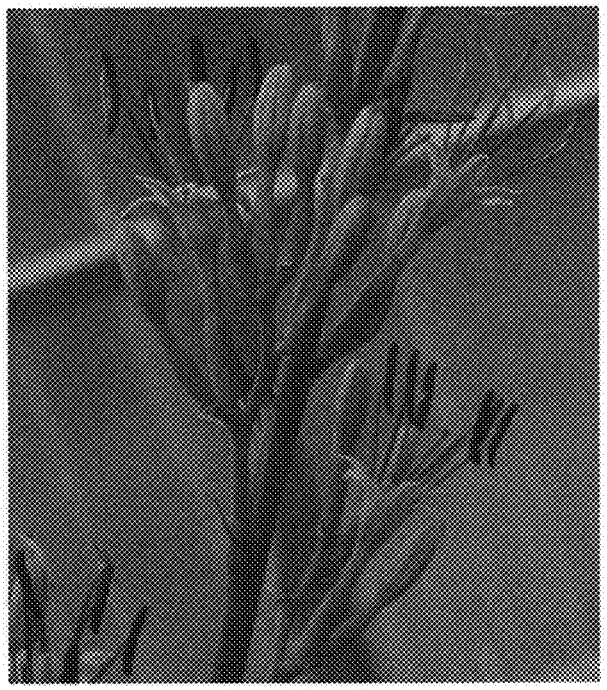
FIG. 2 shows a close-up of the flowers and buds in the upper scape.

The following descriptions and color references are based on the 2015 edition of The Royal Horticultural Society Colour Chart except where common dictionary terms are used. The new plant, X *Mangave* 'Freckles and Speckles', has not been observed under all possible environments. The phenotype may vary slightly with different environmental conditions, such as temperature, light, fertility, moisture and maturity levels, but without any change in the genotype. The following observations and size descriptions are of two and three-year old plants in a commercial wholesale greenhouse in Zeeland, Mich. with supplemental water and fertilizer as needed.

Botanical classification: X *Mangave* hybrid;

Variety denomination: 'Freckles and Speckles';

Parentage: H10-02-01 as the female or seed parent and 12-06-01 as the male or pollen parent;

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 60 fleshy leaves radially emerging and arching from central rhizome, producing a symmetrical rounded mound;

Plant size: Foliage height about 17.0 cm tall from soil line to the top of the leaves, flowering to about 175.0 cm tall and to about 50.0 cm wide at the widest point at soil line;

Foliage description: Lanceolate; simple, fleshy, glabrous; margins finely dentate with flexible teeth; apex acute with flexible mucro; base truncate, sessile, clasping;

Leaf size: To about 19.5 cm long, about 5.0 cm wide at base and 4.5 mm thick, average about 17.5 cm long, 4.5 cm wide and 4.0 mm thick; usually bi-laterally symmetrical; glabrous and slightly glaucous above and below; spots of variable sizes from about 0.5 mm diameter to about 9.0 mm long and 5.0 mm across; teeth 1.5 mm long and 2.0 mm across at base;

Foliage fragrance: None observed;

Leaf blade color:

*Adaxial* (*young*).—Nearest RHS 147B with speckles between RHS N186B and RHS 187B.

*Abaxial* (*young*).—Nearest RHS 138B with speckles nearest RHS N187A.

*Adaxial* (*mature*).—Nearest RHS 138A, maculate with spots of nearest RHS N186B and with higher ultraviolet exposure blushed in distal two-thirds between RHS 187B and RHS N186C.

*Abaxial* (*mature*).—Base nearest RHS 147C, maculate with spots of nearest RHS 138A.

*Teeth*.—Abaxial and adaxial between RHS 186B and RHS 186C.

Mucro: Flexible; straight, about 5.0 mm long;

Mucro color: Nearest RHS NN155D in the distal 1.0 to 2.0 mm and basal 3.0 to 4.0 mm between RHS 186B and RHS 186C;

Spine texture: Flexible, glabrous, sharply pointed;

Petiole: Sessile;

Veins: Parallel; not distinct;

Peduncle: Terete; glaucous; glabrous; stiff; strong; lightly branched; about 172.0 cm long and 12.0 mm diameter at base and 8.0 mm diameter below first flowers; flowering portion about 60.0 cm tall and about 13.0 cm across; branches to about 7.2 cm long and about 2.5 mm diameter at base; attitude main peduncle and branches upwards, erect;

Peduncle color: Basal portion before flowers nearest RHS N187A, flowering portion nearest RHS 138A;

Pedicel: Terete; glaucous; glabrous; stiff; strong; average about 2.5 mm long and 2.2 mm diameter;

Pedicel color: Nearest RHS 138A;

Cauline leaves: About 13 per scape; lanceolate; simple, fleshy, glabrous; margins finely dentate with flexible teeth; apex narrowly acute with flexible mucro; base truncate, sessile, clasping; proximally about 13.7 cm long and about 1.5 cm wide at base, decreasing distally; color adaxial and abaxial same as basal leaves;

Buds one day prior to opening: Elongated globose; about 4.5 cm long and about 8.0 mm across at mid-tepal, base about 4.0 mm diameter;

Bud color: Nearest RHS 138A in basal portion and distally becoming nearest RHS 160C;

Flower description: Perfect, actinomorphic; about 11.5 cm long and opening to about 4.0 cm across at outside of anthers; lasting about 3 to 4 days per flower; flowering period about three weeks in late winter in Michigan greenhouse; producing abundant nectar; approximately 90 flowers per scape; attitude mostly upright;

Flower fragrance: Faint; slightly sweet;

Tepals: Six in two sets of three; glaucous abaxial and slightly lustrous adaxial; glabrous both adaxial and abaxial; acute apex and fused base; outer set about 4.8 cm long, fused in basal 4.2 cm and about 5.0 mm wide at base; inner set about 4.8 cm long and 6.0 mm wide at fusion; inner set creased along edge where overlapped with outer set while in bud;

Tepal color: Adaxial outer and inner tepal set base nearest RHS 153A with light blushing of nearest RHS 187B; abaxial outer set base nearest RHS 144B with distal non-fused portion blend between RHS 11B and RHS 1A blushed slightly with nearest RHS 187C, abaxial inner set base nearest RHS 144B, margin nearest RHS 4A and center between RHS 150C and RHS 150D blushed with RHS187C toward apex;

Androecium: Six;

*Filaments*.—Six; terete distally, slightly applanate base; stiff and straight; about 4.5 cm long and 1.0 mm diameter at base; color between RHS 186D and RHS 185D and maculate with nearest RHS 187C.

*Anther*.—Dorsifixed; longitudinal; about 1.6 cm long and 2.0 mm diameter before opening; after dehiscence curving backward; color nearest blend between RHS N187A and RHS 183A.

*Pollen*.—Abundant; color nearest RHS 4A.

Gynoecium: Single;

*Style*.—6.5 cm long and 2.0 mm diameter at base; color between RHS 186D and RHS 185D and maculate with nearest RHS 187C.

*Stigma*.—Turbinate, apex tri-lobed; about 2.5 mm tall and 3.5 mm across top; color side nearest RHS 177B; top stigmatic surface in tri-pointed star with color nearest RHS 196A.

*Ovary*.—Inferior.

Fruit: Dehiscent, tri-valved, loculicidal capsule; apex abruptly acute; base slightly tapered; about 2.7 cm long and 1.2 cm across;

Fruit color: When immature nearest RHS N138A; at dehiscence blend between RHS 199C and RHS N199B;

Seed: Flattened, near round; about 5.0 mm long 3.0 mm across and about 1.0 mm thick; color blend between RHS N200A and RHS 202A;

Disease resistance: X *Mangave* 'Freckles and Speckles' has not been observed to be resistant to diseases common to other X *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Freckles and Speckles' as herein described and illustrated.

* * * * *